United States Patent [19]

Ueda et al.

[11] Patent Number: 4,782,055
[45] Date of Patent: Nov. 1, 1988

[54] IMIDAZOPYRIDINE COMPOUNDS USEFUL IN THE TREATMENT OF ULCERS

[75] Inventors: Ikuo Ueda, Toyonaka; Youichi Shiokawa, Ibaraki; Kazuhiko Take, Osaka; Hiromichi Itani, Ikeda, all of Japan

[73] Assignee: Fujisawa Pharmaceutical Co., Ltd., Osaka, Japan

[21] Appl. No.: 942,379

[22] Filed: Dec. 16, 1986

Related U.S. Application Data

[63] Continuation-in-part of Ser. No. 865,331, May 21, 1986.

[30] Foreign Application Priority Data

Dec. 16, 1985 [GB] United Kingdom ................ 8530878
Nov. 20, 1986 [GB] United Kingdom ................ 8627736

[51] Int. Cl.$^4$ .................. A61K 31/435; C07D 471/04
[52] U.S. Cl. ..................... 514/241; 514/242; 514/245; 514/253; 514/300; 544/182; 544/212; 544/215; 544/238; 546/121
[58] Field of Search .............. 546/121; 544/182, 212, 544/215, 238; 514/241, 242, 245, 253, 300

[56] References Cited

U.S. PATENT DOCUMENTS 4,450,164 5/1984 Bristol et al. .

FOREIGN PATENT DOCUMENTS 33094 8/1981 European Pat. Off. .

Primary Examiner—Mary C. Lee
Assistant Examiner—Bernard I. Dentz
Attorney, Agent, or Firm—Oblon, Fisher, Spivak, McClelland & Maier

[57] ABSTRACT

The present invention relates to imidazopyridine compounds of the formula:

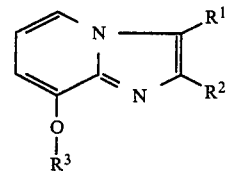

wherein
$R^1$ is lower alkynyl or lower alkynyloxy(lower)-alkyl,
$R^2$ is lower alkyl, and
$R^3$ is ar(lower)alkyl having lower alkoxy, lower alkylthio, nitro or lower alkanesulfonyl, ar(lower)alkyl having nitro and one or two additional substituent(s) selected from nitro and lower alkyl, or heterocyclic(lower)alkyl which may have suitable substituent(s), and to their utility.

The compounds have antiulcerative properties.

14 Claims, No Drawings

IMIDAZOPYRIDINE COMPOUNDS USEFUL IN THE TREATMENT OF ULCERS

This application is a continuation-in-part of application Ser. No. 865,331, filed May 21, 1986.

The present invention relates to novel imidazopyridine compounds and pharmaceutically acceptable salts thereof. More particularly, it relates to novel imidazopyridine compounds and pharmaceutically acceptable salts thereof which have antiulcerative activity, to processes for preparation thereof, to pharmaceutical composition comprising the same, and to method of using the same therapeutically in the treatment of ulcer in human being or animals.

Accordingly, one object of the present invention is to provide novel imidazopyridine compounds and pharmaceutically acceptable salt thereof, which are useful as a medicine for ulcer.

Another object of the present invention is to provide processes for preparation of said imidazopyridine compounds and pharmaceutically acceptable salts thereof.

A further object of the present invention is to provide pharmaceutical composition comprising, as an active ingredient, said imidazopyridine compound or its pharmaceutically acceptable salt.

Still further object of the present invention is to provide method of using said imidazopyridine compound or its pharmaceutically acceptable salt in the treatment of ulcer in human being or animals.

The imidazopyridine compounds of the present invention are novel and can be represented by the formula (I):

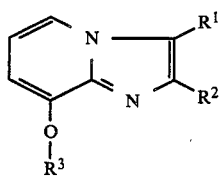

(I)

wherein
$R^1$ is lower alkynyl or lower alkynyloxy(lower)alkyl,
$R^2$ is lower alkyl, and
$R^3$ is ar(lower)alkyl having lower alkoxy, lower alkylthio, nitro or lower alkanesulfonyl, ar(lower)alkyl having nitro and one or two additional substituent(s) selected from nitro and lower alkyl, or heterocyclic(lower)alkyl which may have suitable substituent(s).

According to the present invention, the object compound (I) can be prepared by the following processes.

Process 1

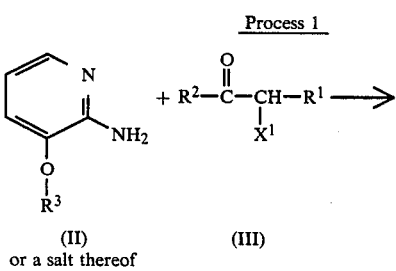

(II)            (III)
or a salt thereof

Process 1

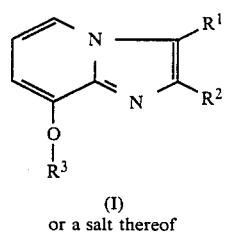

(I)
or a salt thereof

Process 2

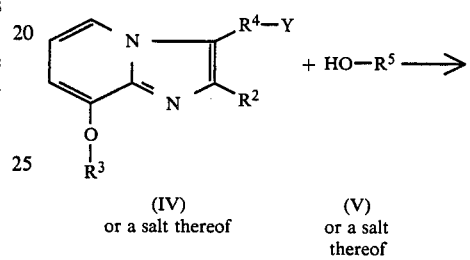

(IV)            (V)
or a salt thereof    or a salt thereof

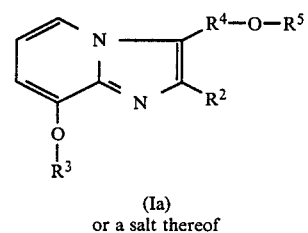

(Ia)
or a salt thereof

Process 3

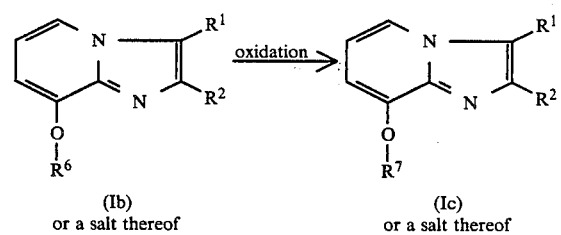

(Ib)            (Ic)
or a salt thereof    or a salt thereof

Process 4

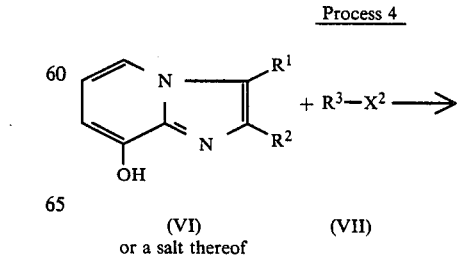

(VI)            (VII)
or a salt thereof

-continued

Process 4

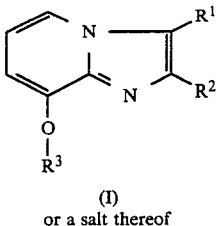

(I)

or a salt thereof wherein

R$^1$, R$^2$ and R$^3$ are each as defined above,

R$^4$ is lower alkylene,

R$^5$ is lower alkynyl,

R$^6$ is ar(lower)alkyl which has lower alkylthio,

R$^7$ is ar(lower)alkyl which has lower alkanesulfonyl,

X$^1$ and X$^2$ are each an acid residue, and

Y is a leaving group.

As to the starting compounds (II), (III), (IV) and (VI), some of them are novel and can be prepared by the procedures disclosed in the following Preparations 1 to 19.

Suitable pharmaceutically acceptable salts of the object compounds (I) are conventional non-toxic salts and include an organic acid salt (e.g. acetate, maleate, tartrate, methanesulfonate, benzenesulfonate, formate, toluenesulfonate, etc.), an inorganic acid salt (e.g. hydrochloride, hydrobromide, sulfate, phosphate, etc.), a salt with an amino acid (e.g., arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

Suitable "lower alkynyl" and suitable "lower alkynyl moiety" in the term "lower alkynyloxy(lower)alkyl" may be the ones having 2 to 6 carbon atoms and may include ethynyl, 1(or 2)-propynyl, 1(or 2 or 3)-butynyl, 1(or 2 or 3 or 4)-pentynyl, 1(or 2 or 3 or 4 or 5)-hexynyl and the like.

Suitable "lower alkyl" and suitable "lower alkyl moiety" in the terms "lower alkynyloxy(lower)alkyl" and "heterocyclic(lower)alkyl" may be the ones having 1 to 6 carbon atom(s) and may include methyl, ethyl, propyl, isopropyl, n-butyl, t-butyl, pentyl, hexyl and the like.

Suitable "ar(lower)alkyl" may include mono(or di or tri)-phenyl(lower)alkyl such as benzyl, benzyhydryl, trityl, phenethyl or the like.

Suitable "heterocyclic moiety" in the term "heterocyclic(lower)alkyl" may be 3 to 7 membered (more preferably 5 or 6 membered) heteromonocyclic group having 1 to 3 hetero atom(s) such as thienyl, furyl, pyrrolyl, pyrazolyl, thiazolyl, thiadiazolyl, triazolyl, pyridyl, pyridazinyl, triazinyl or the like.

Said "heterocyclic(lower)alkyl" may have one or more, preferably one to three suitable substituent(s) such as lower alkyl (e.g. methyl, ethyl, propyl, n-butyl, t-butyl, pentyl, hexyl, etc.), lower alkoxy (e.g. methoxy, ethoxy, propoxy, butoxy, t-butoxy, pentyloxy, hexyloxy, etc.), acylamino such as lower alkanamido (e.g. formamido, acetamido, etc.) or the like.

Suitable "lower alkylene" may include methylene, ethylene, trimethylene, tetramethylene, pentamethylene, hexamethylene and the like.

Suitable "an acid residue" may include halogen (e.g. fluorine, chlorine, bromine, iodine), acyloxy (e.g. acetoxy, tosyloxy, mesyloxy, etc.) and the like.

Suitable "lower alkoxy" may include methoxy, ethoxy, propoxy, butoxy, t-butoxy, pentyloxy, hexyloxy and the like.

Suitable "lower alkylthio" may include methylthio, ethylthio, propylthio, butylthio, t-butylthio, pentylthio, hexylthio and the like.

Suitable "lower alkanesulfonyl" may include mesyl, ethanesulfonyl, propanesulfonyl, butanesulfonyl, t-butanesulfonyl, pentanesulfonyl, hexanesulfonyl and the like.

Suitable "a leaving group" may include an acid residue as mentioned above, a group of the formula:

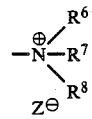

wherein

R$^6$, R$^7$ and R$^8$ are each lower alkyl as mentioned above, and

Z is an acid residue as mentioned above, and the like.

Preferred embodiments of the object compounds (I) are as follows.

Preferred embodiment of R$^1$ is lower alkynyl, more preferably C$_2$-C$_3$ alkynyl; or lower alkynyloxy(lower)alkyl, more preferably C$_2$-C$_3$ alkynyloxy(C$_1$-C$_3$)alkyl.

Preferred embodiment of R$^2$ is lower alkyl, more preferably C$_1$-C$_3$ alkyl.

Preferred embodiment of R$^3$ is phenyl(lower)alkyl having lower alkoxy, more preferably phenyl(C$_1$-C$_3$)alkyl having (C$_1$-C$_3$)alkoxy; phenyl(lower)alkyl having lower alkylthio, more preferably phenyl(C$_1$-C$_3$)alkyl having (C$_1$-C$_3$)alkylthio; phenyl(lower)alkyl having nitro, more referably phenyl(C$_1$-C$_3$)alkyl having nitro; phenyl(lower)alkyl having lower alkanesulfonyl, more preferably phenyl(C$_1$-C$_3$)alkyl having (C$_1$-C$_3$)alkanesulfonyl; 3 to 7 membered heteromonocyclic(lower)alkyl which may have lower alkyl, more preferably 5 or 6 membered heteromonocyclic(C$_1$-C$_3$)alkyl which may have (C$_1$-C$_3$)alkyl; 3 to 7 membered heteromonocyclic(lower)alkyl which may have lower alkoxy, more preferably 5 or 6 membered heteromonocyclic(C$_1$-C$_3$)alkyl which may have (C$_1$-C$_3$)alkoxy; 3 to 7 membered heteromonocyclic(lower)alkyl which may have acylamino, more preferably 5 or 6 membered heteromonocyclic(C$_1$-C$_3$)alkyl which may have (C$_1$-C$_3$)alkanoylamino; phenyl(lower)alkyl having nitro and lower alkyl, more preferably phenyl(C$_1$-C$_3$)alkyl having nitro and (C$_1$-C$_3$)alkyl; or phenyl(lower)alkyl having nitro and two lower alkyl, more preferably phenyl(C$_1$-C$_3$)alkyl having nitro and two (C$_1$-C$_3$)alkyl.

The processes for preparing the object compounds of the present invention are explained in detail in the following.

Process 1

The object compound (I) or a salt thereof can be prepared by reacting the compound (II) or a salt thereof with the compound (III).

Suitable salts of the compound (II) can be referred to the acid addition salt as exemplified for the compound (I).

This reaction is usually carried out in a solvent such as alcohol [e.g. methanol, ethanol, etc.], benzene, N,N-dimethylformamide, tetrahydrofuran, diethyl ether or any other solvent which does not adversely affect the reaction.

The reaction may be carried out in the presence of an inorganic or an organic base such as an alkali metal hydroxide [e.g. sodium hydroxide, potassium hydroxide, etc.], an alkali metal carbonate [e.g. sodium carbonate, potassium carbonate etc.], an alkali metal bicarbonate [e.g. sodium bicarbonate, potassium bicarbonate, etc.], tri(lower)alkylamine [e.g. trimethylamine, triethylamine, etc.], pyridine or its derivative [e.g., picoline, lutidine, 4-dimethylaminopyridine, etc.], or the like. In case that the base to be used is liquid, it can also be used as a solvent.

The reaction temperature is not critical, and the reaction can be carried out under cooling, at ambient temperature or under warming or heating.

Process 2

The object compound (Ia) or a salt thereof can be prepared by reacting the compound (IV) or a salt thereof with the compound (V) or a salt thereof.

Suitable salts of the compounds (IV) and (Ia) can be referred to the ones as exemplified for the object compound (I).

Suitable salts of the compound (V) are salts with a base such as an alkali metal salt (e.g. sodium salt, potassium salt, lithium salt, etc.) or the like.

This reaction is usually carried out in the presence of a base such as alkali metal hydride (e.g. sodium hydride, potassium hydride, lithium hydride, etc.), alkali metal alkoxide (e.g. potassium t-butoxide, etc.), an alkali metal (e.g. sodium, potassium, lithium, etc.) or the like.

This reaction is usually carried out in a solvent such as alcohol [e.g. methanol, ethanol, etc.], dimethyl sulfoxide, benzene, N,N-dimethylformamide, tetrahydrofuran, diethyl ether or any other solvent which does not adversely affect the reaction.

In case that the compound (V) or a salt thereof to be used is liquid, it can also be used as a solvent.

The reaction temperature is not critical, and the reaction can be carried out under cooling, at ambient temperature or under warming or heating.

Process 3

The object compound (Ic) or a salt thereof can be prepared by subjecting the compound (Ib) or a salt thereof to oxidation reaction.

Suitable salts of the compounds (Ib) and (Ic) can be referred to the ones as exemplified for the object compound (I).

Suitable example of oxidizing agent to be used in this reaction may include all oxidizing agents, which can oxidize —S— group to —$SO_2$— group and do not adversely affect the compounds (Ib) or (Ic), for example, peroxy-acid such as hydrogen peroxide, perbenzoic acid, perphthalic acid, performic acid, peracetic acid, trifluoroperacetic acid, m-chloroperbenzoic acid or the like.

This reaction is usually carried out in a solvent such as acetic acid, chloroform, methylene chloride, diethyl ether, dioxane, benzene or any other solvent which does not adversely affect the reaction.

The reaction temperature is not critical and the reaction is usually carried out under cooling, at ambient temperature, under warming or heating.

Process 4

The object compound (I) or a salt thereof can be prepared by reacting the compound (VI) or a salt thereof with the compound (VII).

Suitable salts of the compound (VI) can be referred to the salt as exemplified for the compound (I).

This reaction is usually carried out in a solvent such as alcohol [e.g. methanol, ethanol, etc.], benzene, N,N-dimethylformamide, tetrahydrofuran, diethyl ether or any other solvent which does not adversely affect the reaction.

The reaction may be carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], tri(lower)alkylamine [e.g. trimethylamine, triethylamine, etc.], pyridine or its derivative [e.g. picoline, lutidine, 4-dimethylaminopyridine, etc.], or the like. In case that the base to be used is liquid, it can also be used as a solvent.

The reaction temperature is not critical, and the reaction can be carried out under cooling, at ambient temperature or under warming or heating.

The object compounds (I) and their pharmaceutically acceptable salts of the present invention are novel and exhibit high inhibitory activity on ulcer.

In order to illustrate the usefulness of the object compound (I), the pharmacological data of the representative compound of the object compounds (I) are shown in the following.

(A) Inhibition on ethanol ulcer

Test Method:

Five male Sprague-Dawley rats, aged 7 weeks and weighing about 200 g, were used per group for the study on ethanol ulcer after the fast for 24 hours.

Test compound was suspended in 0.1% methylcellulose aqueous solution, and the suspension (5 ml/kg) was orally given to each rat.

The control group was given a vehicle, i.e. 0.1% methylcellulose aqueous solution (5 ml/kg), alone in the same way.

Absolute ethanol (5 ml/kg) was orally administered 30 minutes after dosing with test compound, and one hour later, the rats were sacrificed and their stomachs were removed. The area of ulcers of each rat was measured. The mean area (mm) in the medicated group was compared with that in the control group.

Test Compounds (1) 8-(2-Methoxybenzyloxy)-2-methyl-3-(2-propynyloxymethyl)imidazo[1,2-a]pyridine Test Result Inhibition % at the dose of 32 mg/kg:

| Test Compound | Inhibition % |
|---|---|
| (1) | 95.7 |

(B) Inhibition on stress ulcer

Test Method:

Five Sprague-Dawley rats weighing about 200 g were used per group. Each animal was immobilized in a small cage and put in a water bath allowing to respire. The temperature of the water bath kept as 22° C. The test compound was administered orally just before the immobilization. Seven hours later, the animals were sacrificed and their stomachs were removed. The stomach was then fixed with 2% formalin. The area of ulcers was measured for each animal. The mean area (mm²) in the medicated animals was compared with that in the control animals.

Test Compounds (1) 8-(2-Methoxybenzyloxy)-2-methyl-3-(2-propynyl-)imidazo[1,2-a]pyridine Test Result Inhibition % at the dose of 32 mg/kg:

| Test Compound | Inhibition % |
|---|---|
| (1) | 100 |

As being apparent from the above test results, the object compound (I) of the present invention are useful as antiulcer medicines.

For therapeutic purpose, the compounds according to the present invention can be used in a form of pharmaceutical preparation containing said compound as an active ingredient, in admixture with a pharmaceutically acceptable carrier such as an organic or inorganic solid liquid excipient suitable for oral or parenteral administration. The pharmaceutical preparations may be capsules, tablets, dragees, solution, suspension, emulsion, and the like. If desired, there may be included in the above preparations auxiliary substances, stabilizing agents, wetting or emulsifying agents, buffers and other commonly used additives.

While the dosage of the compounds will vary depending upon the age and condition of the patient, n average single dose of about 5 mg, 10 mg, 50 mg, 100 mg, 250 mg, 500 mg, and 1000 mg of the compounds according to the present invention may be effective for treating ulcer. In general, amounts between 1 mg/body and about 2,000 mg/body or even more may be administered per day.

The following preparations and examples are given for the purpose of illustrating the present invention.

Preparation 1

Tosyl chloride (3.81 g) was added to a solution of 3-hydroxy-5-hexyn-2-one (2.24 g) and triethylamine (2.424 g) in methylene chloride (20 ml) under ice-cooling. After being stirred for 2.5 hours, the mixture was washed with water, dried over magnesium sulfate and evaporated in vacuo. The oily residue was purified by column chromatography on silica gel (60 g) using methylene chloride as an eluent to give an oil of 3-tosyloxy-5-hexyn-2-one (2.94 g).

IR (film/NaCl): 3280, 1720, 1590, 1360 (broad) cm$^{-1}$.

NMR (CCl$_4$, δ): 1.79 (1H, t, J=2 Hz), 2.25 (3H, s), 2.43 (3H, s), 2.3–2.6 (2H, m), 4.66 (1H, t, J=5 Hz), 7.31 (2H, d, J=8 Hz), 7.78 (2H, d, J=8 Hz).

Preparation 2

To a mixture of 2-amino-3-hydroxypyridine (7.64 g) and Adogen 464 (Trademark: prepared by Aldrich Chemical Co.) (0.42 g) in 40% aqueous sodium hydroxide (35 ml) and methylene chloride (35 ml) was added 2-methoxybenzyl chloride (10.87 g) at ambient temperature. After being stirred for 22 hours, the organic layer was separated and the aqueous layer was extracted with methylene chloride. The combined extracts were washed with saturated sodium chloride aqueous solution, dried over magnesium sulfate, and evaporated in vacuo. The crystalline residue was recrystallized from ethyl acetate to give 2-amino-3-(2-methoxybenzyloxy)-pyridine (6.09 g).

mp: 111° to 113° C. (recrystallized from a mixture of methylene chloride and diisopropyl ether).

IR (Nujol): 3430, 3205, 3180, 1627 cm$^{-1}$.

NMR (CDCl$_3$, δ): 3.81 (3H, s), 4.82 (2H, broad s), 5.08 (2H, s), 6.52 (1H, dd, J=4 Hz and 7 Hz), 6.80–7.09 (3H, m), 7.17–7.46 (2H, m), 7.62 (1H, d, J=4 Hz).

Preparation 3

The following compounds were prepared according to a similar manner to that of Preparation 2.

(1) 2-Amino-3-(2-methylthiobenzyloxy)pyridine mp: 101° to 103° C. (recrystallized from a mixture of ethyl acetate and n-hexane).

IR (Nujol): 3450, 3270, 3145, 1620 cm$^{-1}$.

NMR (CDCl$_3$, δ): 2.47 (3H, s), 4.78 (2H, broad s), 5.12 (2H, s), 6.44–6.68 (1H, m), 6.99 (1H, d, J=7 Hz), 7.11–7.50 (4H, m), 7.67 (1H, dd, J=2 Hz and 5 Hz).

(2) 2-Amino-3-(2-nitrobenzyloxy)pyridine mp: 139° to 141° C. (recrystallized from chloroform)

IR (Nujol): 3450, 3260, 3100, 1625, 1520, 1350 cm$^{-1}$.

NMR (DMSO-d$_6$, δ): 5.50 (2H, s), 5.73 (2H, broad s), 6.40–6.66 (1H, m), 7.12 (1H, dd, J=2 Hz and 10 Hz), 7.46–8.30 (5H, m).

Preparation 4

To a solution of 2-amino-3-hydroxypyridine (15.18 g) in N,N-dimethylformamide (150 ml) was added portionwise a 60% dispersion of sodium hydride in mineral oil (6.06 g) with ice-cooling and stirring over a period of 10 minutes. After being stirred at 0°–5° C. for 30 minutes and then at ambient temperature for 1 hour, a solution of 2-chloromethyl-3-methylthiophene (23.9 g) in N,N-dimethylformamide (10 ml) was added dropwise to the reaction mixture. The mixture was stirred at ambient temperature for 20 hours and poured into water. The resulting precipitate was collected by filtration and dissolved in methylene chloride. The solution was treated with activated charcoal and evaporated in vacuo. The residue was crystallized from diethyl ether to give 2-amino-3-(3-methyl-2-thienylmethoxy)pyridine (23.6 g).

mp: 131° to 132.5° C.

IR (Nujol): 3480, 3280, 3100, 1625 cm$^{-1}$.

NMR (DMSO-d$_6$, δ): 2.25 (3H, s), 5.18 (2H, s), 5.52 (2H, broad s), 6.36–6.66 (1H, m), 6.89 (1H, d, J=5 Hz), 7.13 (1H, dd, J=1 Hz and 8 Hz), 7.41 (1H, d, J=5 Hz), 7.54 (1H, dd, J=2 Hz and 5 Hz).

Preparation 5

A 60% dispersion of sodium hydride in mineral oil (0.3 g) was added portionwise to a suspension of 8-hydroxy-2-methylimidazo[1,2-a]pyridine (1.0 g) in dimethyl sulfoxide (10 ml) at room temperature over a period of 15 minutes. After being stirred for 30 minutes, 4-nitrobenzyl bromide (1.6 g) was added in one portion to the mixture and then the resultant mixture was stirred for 24 hours at room temperature. The mixture was poured into water and the resulting precipitate was collected by filtration. The crude product was purified by column chromatography on silica gel (30 g) with methylene chloride as an eluent to afford a solid, which was recrystallized from a mixture of ethyl acetate and n-hexane to give 2-methyl-8-(4-nitrobenzyloxy)imidazo[1,2-a]pyridine (0.77 g).

mp: 160° to 165° C.

NMR (CDCl$_3$, δ): 2.50 (3H, s), 5.40 (2H, s), 6.20–6.70 (2H, m), 7.33 (1H, s), 7.46–7.80 (3H, m), 8.16 (2H, d, J=8 Hz).

Preparation 6

The following compounds were prepared according to a similar manner to that of Preparation 5.

(1) 8-(2-Methoxybenzyloxy)-2-methylimidazo[1,2-a]pyridine

NMR (CDCl$_3$, δ): 2.46 (3H, s), 3.85 (3H, s), 5.36 (2H, s), 6.23–6.66 (2H, m), 6.72–7.06 (2H, m), 7.10–7.36 (2H, m), 7.37–7.70 (2H, m).

(2) 2-Methyl-8-(2-nitrobenzyloxy)imidazo[1,2-a]pyridine mp: 158° to 160° C. (recrystallized from ethanol)

NMR (CDCl$_3$, δ): 2.49 (3H, s), 5.73 (2H, s), 6.26–6.76 (2H, m), 7.25–7.83 (4H, m), 7.96 (1H, s), 8.15 (1H, dd, J=2 Hz, 8 Hz).

Preparation 7

To a solution of 37% aqueous formaldehyde (1.57 g) in acetic acid (25 ml) was added dropwise 50% aqueous dimethylamine (1.75 g) with ice-cooling over a period of 10 minutes and the mixture was stirred for an additional 10 minutes. The mixture was heated at 50°–55° C. for 2 hours after an addition of 8-(2-methoxybenzyloxy)-2-methylimidazo[1,2-a]pyridine (4.96 g) thereto and then evaporated in vacuo. The residue was basified with aqueous sodium hydroxide and extracted with methylene chloride. The extract was washed with water, dried over magnesium sulfate and evaporated in vacuo. The residual solid was recrystallized from diethyl ether to give 3-dimethylaminomethyl-8-(2-methoxybenzyloxy)-2-methylimidazo[1,2-a]pyridine (3.55 g).

mp: 139° to 141° C.

NMR (CDCl$_3$, δ): 2.20 (6H, s), 2.43 (3H, s), 3.58 (2H, s), 3.83 (3H, s), 5.33 (2H, s), 6.35–6.69 (6H, m), 6.89 (2H, t, J=5 Hz), 7.13–7.36 (1H, m), 7.52 (1H, b.d, J=5 Hz), 7.76 (1H, dd, J=1 Hz, 4 Hz).

Preparation 8

The following compound was prepared according to a similar manner to that of Preparation 7.

3-Dimethylaminomethyl-2-methyl-8-(2-nitrobenzyloxy)imidazo[1,2-a]pyridine mp: 160° to 162° C.

NMR (CDCl$_3$, δ): 2.20 (6H, s), 2.46 (3H, s), 3.60 (2H, s), 5.72 (2H, s), 6.30–6.80 (2H, m), 7.23–8.06 (4H, m), 8.16 (1H, dd, J=2 Hz, 7 Hz).

Preparation 9

Methyl iodide (1.08 g) was added dropwise to a solution of 3-dimethylaminomethyl-8-(2-methoxybenzyloxy)-2-methylimidazo[1,2-a]pyridine (3.42 g) in acetone (34 ml) and chloroform (10 ml) at room temperature and the mixture was stirred for 24 hours. The resulting precipitate was collected by filtration, washed with acetone, and dried in a desiccator to give 8-(2-methoxybenzyloxy)-2-methyl-3-trimethylammoniomethylimidazo[1,2-a]pyridine iodide (3.63 g).

mp: >160° C. (dec.).

NMR (DMSO-d$_6$, δ): 2.49 (3H, s), 3.19 (9H, s), 3.86 (3H, s), 5.08 (2H, s), 5.27 (2H, s), 6.83–7.60 (6H, m), 8.35–8.61 (1H, m).

Preparation 10

The following compound was prepared according to a similar manner to that of Preparation 9.

2-Methyl-8-(2-nitrobenzyloxy)-3-trimethylammoniomethylimidazo[1,2-a]pyridine iodide mp: >163° C. (dec.).

NMR (DMSO-d$_6$, δ): Ca 2.4–2.7 (3H, s), 3.11 (9H, s), 4.99 (2H, s), 5.69 (2H, s), 6.80–7.10 (2H, m), 7.63–8.00 (2H, m), 8.06–8.56 (3H, m).

Preparation 11

The following compound was prepared according to a similar manner to that of Preparation 2.

2-Amino-3-methoxymethoxypyridine

NMR (CDCl$_3$, δ): 3.50 (3H, s), 4.40–5.13 (2H, br s), 5.20 (2H, s), 6.46–6.76 (1H, m), 7.20 (1H, dd, J=2 Hz, 8 Hz), 7.73 (1H, dd, J=2 Hz, 5 Hz).

Preparation 12

A solution of 2-amino-3-methoxymethoxypyridine (7.5 g) and 3-mesyloxy-5-hexyn-2-one (10.18 g), in ethanol (150 ml) was refluxed for 46.5 hours and then evaporated in vacuo. To the residue was added 20% sulfuric acid (75 ml) and the mixture was stirred for 5 hours at room temperature. The mixture was made alkaline with sodium bicarbonate and extracted with chloroform. The extract was washed with brine, dried over magnesium sulfate, and evaporated in vacuo. The residue was purified by column chromatography on silica gel (30 g) with chloroform and then a mixture of chloroform and methanol (30:1 to 20:1) as eluents. The eluates were evaporated in vacuo and the residue was recrystallized from a mixture of ethyl acetate and n-hexane to give 8-hydroxy-2-methyl-3-(2-propynyl)imidazo[1,2-a]pyridine (1.93 g).

mp: 175° to 177° C.

NMR (CDCl$_3$, δ): 2.03 (1H, t, J=3 Hz), 2.45 (3H, s), 3.73 (2H, d, J=3 Hz), 6.70–6.90 (2H, m), 7.57–7.76 (1H, m), 11.29 (1H, s).

Preparation 13

A mixture of 2,6-dimethylbenzyl alcohol (8.17 g) and acetic anhydride (8.1 g) was heated at 70° C. for 3 hours and evaporated in vacuo. To the residue was added aqueous sodium bicarbonate and extracted with diethyl ether. The extract was washed with water, dried over magnesium sulfate, and evaporated in vacuo to give an oil of 2,6-dimethylbenzyl acetate (10.75 g).

IR (film): 1720, 1590, 1470, 1380, 1230, 1020 cm$^{-1}$.

NMR (CDCl$_3$, δ): 2.05 (3H, s), 2.37 (6H, s), 5.20 (2H, s), 6.90–7.33 (3H, s).

Preparation 14

Fuming nitric acid (0.52 ml) was added dropwise to a solution of 2,6-dimethylbenzyl acetate (1.78 g) in acetic anhydride (8.9 ml) at 0° C. and then stirred for 2.5 hours. After being stirred for an additional 30 minutes at room temperature, the mixture was poured onto crushed ice, neutralized with sodium bicarbonate, and extracted with ethyl acetate. The extract was washed with water and evaporated in vacuo. To the residue were added methanol (24 ml) and 1N sodium hydroxide solution (12 ml) and the mixture was stirred at room temperature for 1 hour and evaporated in vacuo. The residue was washed with water, air-dried, and recrystallized from a mixture of benzene and n-hexane to give 2,6-dimethyl-3-nitrobenzyl alcohol (1.26 g).

mp: 94° to 95° C.
IR (Nujol): 3125, 1580, 1510, 1385, 995 cm$^{-1}$.
NMR (CDCl$_3$, δ): 2.50 (3H, s), 2.55 (3H, s), 4.80 (2H, s), 7.17 (2H, d, J=8 Hz), 7.67 (2H, d, J=8 Hz).

Preparation 15

2,6-Dimethyl-3-nitrobenzyl chloride was obtained from 2,6-dimethyl-3-nitrobenzyl alcohol according to a conventional manner.

mp: 54° to 55° C. (recrystallized from cyclohexane).
IR (Nujol): 1595, 1520, 1385, 1270 cm$^{-1}$.
NMR (CDCl$_3$, δ): 2.52 (3H, s), 2.57 (3H, s), 4.68 (2H, s), 7.17 (1H, d, J=8 Hz), 7.87 (1H, d, J=8 Hz).

Example 1

A solution of 2-amino-3-(2-methoxybenzyloxy)pyridine (3.50 g) and 3-tosyloxy-5-hexyn-2-one (4.86 g) in ethanol (30 ml) was stirred and refluxed for 24 hours and then evaporated in vacuo. To the residue was added an aqueous solution of sodium bicarbonate and the mixture was extracted with ethyl acetate. The extract was washed with water, dried over magnesium sulfate and evaporated in vacuo. The oily residue was purified by column chromatography on silica gel (50 g) using chloroform as an eluent to give a solid, which was recrystallized from a mixture of ethyl acetate and n-hexane to give 8-(2-methoxybenzyloxy)-2-methyl-3-(2-propynyl)imidazo[1,2-a]pyridine (1.49 g).

mp: 134° to 136° C.
IR (Nujol): 3365, 3280 cm$^{-1}$.
NMR (CDCl$_3$, δ): 2.03 (1H, t, J=3 Hz), 2.46 (3H, s), 3.72 (2H, d, J=3 Hz), 3.83 (3H, s), 5.36 (2H, s), 6.36–6.73 (2H, m), 6.74–7.02 (2H, m), 7.13–7.41 (1H, m), 7.44–7.59 (1H, m), 7.64 (1H, dd, J=2 Hz and 7 Hz).
Analysis Calcd. for C$_{19}$H$_{18}$N$_2$O$_2$: C 74.49; H 5.92; N 9.14; Found: C 74.85; H 5.97; N 9.15.

Example 2

The following compounds were prepared according to a similar manner to that of Example 1.

(1) 2-Methyl-8-(2-methylthiobenzyloxy)-3-(2-propynyl)imidazo[1,2-a]pyridine mp: 130° to 132° C. (recrystallized from a mixture of ethyl acetate and n-hexane).
IR (Nujol): 3270 cm$^{-1}$.
NMR (CDCl$_3$, δ): 2.06 (1H, t, J=3 Hz), 2.46 (3H, s), 2.49 (3H, s), 3.75 (2H, d, J=3 Hz), 5.39 (2H, s), 6.43 (1H, d, J=8 Hz), 6.64 (1H, t, J=8 Hz), 7.02–7.38 (3H, m), 7.50–7.98 (1H, m), 8.03 (1H, d, J=8 Hz).
Analysis Calcd. for C$_{19}$H$_{18}$N$_2$OS: C 70.78; H 5.63; N 8.69; Found: C 70.96; H 5.63; N 8.60.

(2) 2-Methyl-8-(2-nitrobenzyloxy)-3-(2-propynyl)imidazo[1,2-a]pyridine mp: 176.5° to 177.5° C. (recrystallized from ethanol).
IR (Nujol): 3100, 1545, 1510 cm$^{-1}$.
NMR (DMSO-d$_6$, δ): 2.36 (3H, s), 2.93 (1H, t, J=2 Hz), 3.92 (2H, d, J=2 Hz), 5.70 (2H, s), 6.63–6.99 (2H, m), 7.43–8.06 (4H, m), 8.15 (1H, dd, J=2 Hz and 6 Hz).
Analysis Calcd. for C$_{18}$H$_{15}$N$_3$O$_3$: C 67.28; H 4.70; N 13.08; Found: C 67.63; H 5.18; N 13.03.

(3) 2-Methyl-8-(3-methyl-2-thienylmethoxy)-3-(2-propynyl)imidazo[1,2-a]pyridine mp: 112° to 113° C. (recrystallized from a mixture of diethyl ether and n-hexane).
IR (Nujol): 3300, 1530 cm$^{-1}$.
NMR (CDCl$_3$, δ): 2.03 (1H, t, J=3 Hz), 2.27 (3H, s), 2.43 (3H, s), 3.73 (2H, d, J=3 Hz), 5.39 (2H, s), 6.48–6.75 (2H, m), 6.82 (1H, d, J=5 Hz), 7.19 (1H, d, J=5 Hz), 7.72 (1H, dd, J=1.5 Hz and 6 Hz).
Analysis Calcd. for C$_{17}$H$_{16}$N$_2$OS: C 68.89; H 5.44; N 9.45; Found: C 68.86; H 5.06; N 9.44.

(4) 2-Methyl-3-(2-propynyl)-8-(3-pyridylmethoxy)imidazo[1,2-a]pyridine mp: 140° to 142° C. (recrystallized from ethyl acetate).
IR (Nujol): 3600–3200 (broad), 3310, 1585, 1540 cm$^{-1}$.
NMR (CDCl$_3$, δ): 1.96–2.16 (1H, m), 2.46 (3H, s), 3.74 (2H, d, J=3 Hz), 5.33 (2H, s), 6.34–6.81 (2H, m), 7.11–7.40 (1H, m), 7.60–8.0 (2H, m), 8.52 (1H, dd, J=2 Hz and 5 Hz), 8.68 (1H, d, J=2 Hz).
Analysis Calcd. for C$_{17}$H$_{15}$N$_3$O: C 73.63; H 5.45; N 15.15; Found: C 73.35; H 5.40; N 14.73.

(5) 8-(2-Mesylbenzyloxy)-3-(2-propynyl)-2-methylimidazo[1,2-a]pyridine mp: 179° to 180° C.

Example 3

A solution of m-chloroperbenzoic acid (4.53 g) in methylene chloride (56 ml) was added dropwise to a solution of 2-methyl-8-(2-methylthiobenzyloxy)-3-(2-propynyl)imidazo[1,2-a]pyridine (2.4 g) in methylene chloride (72 ml) with ice-cooling and stirring over a period of 10 minutes. After being stirred for 93 hours at ambient temperature, the solution was washed successively with aqueous sodium bicarbonate, water, and saturated sodium chloride aqueous solution, dried over magnesium sulfate, and evaporated in vacuo. The residue was purified by column chromatography on silica gel (60 g) with chloroform as an eluent to afford a solid, which was recrystallized from a mixture of ethanol and tetrahydrofuran to give 8-(2-mesylbenzyloxy)-2-methyl-3-(2-propynyl)imidazo[1,2-a]pyridine (0.53 g).

mp: 179° to 180° C.
IR (Nujol): 3180 cm$^{-1}$.
NMR (CDCl$_3$, δ): 2.08 (1H, t, J=3 Hz), 2.40 (3H, s), 3.27 (3H, s), 3.75 (2H, d, J=3 Hz), 5.67 (2H, s), 6.56–6.87 (2H, m), 7.41–7.83 (4H, m), 8.03–8.20 (1H, m)
Analysis Calcd. for C$_{19}$H$_{18}$N$_2$O$_3$S: C 64.39; H 5.12; N 7.90; Found: C 64.30; H 4.92; N 7.78.

Example 4

Potassium carbonate (0.52 g) was added to a solution of 8-hydroxy-2-methyl-3-(2-propynyl)imidazo[1,2-a]pyridine (0.5 g) and 4-chloromethyl-3-methylpyridine (0.53 g) in N,N-dimethylformamide (10 ml). The mixture was stirred under a nitrogen atmosphere for 5 hours at room temperature and then poured into water. The resulting precipitates were collected by filtration and recrystallized from ethyl acetate to give 2-methyl-8-(3-methyl-4-pyridylmethoxy)-3-(2-propynyl)imidazo[1,2-a]pyridine (0.58 g).

mp: 156° to 157° C.
NMR (DMSO-d$_6$, δ): 2.36 (6H, s), 2.95 (1H, t, J=3 Hz), 3.93 (2H, d, J=3 Hz), 5.37 (2H, s), 6.70–6.90 (2H, m), 7.49 (1H, d, J=5 Hz), 7.85–8.03 (1H, m), 8.39–8.53 (2H, m).
Analysis Calcd. for C$_{18}$H$_{17}$N$_3$O: C 74.21; H 5.88; N 14.42; Found: C 74.53; H 6.02; N 14.47.

Example 5

The following compounds were prepared according to a similar manner to that of Example 4.

(1) 2-Methyl-8-(2-methyl-3-pyridylmethoxy)-3-(2-propynyl)imidazo[1,2-a]pyridine mp: 167° to 169° C. (recrystallized from ethyl acetate).

NMR (CDCl$_3$, δ): 2.06 (1H, t, J=3 Hz), 2.46 (3H, s), 2.63 (3H, s), 3.78 (2H, d, J=3 Hz), 5.31 (2H, s), 6.36–6.86 (2H, m), 6.98–7.33 (1H, m), 7.65–7.92 (2H, m), 8.43 (1H, dd, J=2 Hz, 5 Hz).

(2) 2-Methyl-8-(3-methyl-2-pyridylmethoxy)-3-(2-propynyl)imidazo[1,2-a]pyridine mp: 133° to 134° C. (recrystallized from a mixture of ethyl acetate and diisopropyl ether).

NMR (CDCl$_3$, δ): 2.05 (1H, t, J=3 Hz), 2.45 (3H, s), 2.52 (3H, s), 3.75 (2H, d, J=3 Hz), 5.46 (2H, s), 6.63–6.86 (2H, m), 7.03–7.80 (3H, m), 8.35–8.56 (1H, m).

Analysis Calcd. for C$_{18}$H$_{17}$N$_3$O: C 74.21; H 5.88; N 14.42; Found: C 74.24; H 5.80; N 14.49.

(3) 8-(2-Acetamidothiazol-4-ylmethoxy)-2-methyl-3-(2-propynyl)imidazo[1,2-a]pyridine mp: 176° to 178° C. (recrystallized from a mixture of ethyl acetate and n-hexane).

NMR (CDCl$_3$, δ): 2.06 (1H, t, J=3 Hz), 2.20 (3H, s), 2.43 (3H, s), 3.75 (2H, d, J=2 Hz), 5.20 (2H, s), 6.43–6.86 (2H, m), 6.95 (1H, s), 7.72 (1H, dd, J=2 Hz, 6 Hz), 11.0–11.60 (1H, br s).

(4) 8-(3,5-Dimethyl-4-methoxy-2-pyridylmethoxy)-2-methyl-3-(2-propynyl)imidazo[1,2-a]pyridine mp: 158° to 159° C. (recrystallized from a mixture of ethanol and diisopropyl ether).

IR (Nujol): 3225, 1565, 1545, 1405, 1290 cm$^{-1}$.

NMR (CDCl$_3$, δ): 2.05 (1H, t, J=3 Hz), 2.27 (3H, s), 2.42 (3H, s), 2.43 (3H, s), 3.76 (2H, m), 3.77 (3H, s), 5.40 (2H, s), 6.53–6.90 (2H, m), 7.67 (1H, dd, J=2 Hz, 6 Hz), 8.23 (1H, s).

Example 6

To a solution of sodium hydride (63.6% in mineral oil dispersion, 0.282 g) in 2-propynyl alcohol (14 ml) was added 8-(2-methoxybenzyloxy)-2-methyl-3-trimethylammoniomethylimidazo[1,2-a]pyridine iodide (3.43 g) and the mixture was heated at 90°–95° C. with stirring for 1 hour. After being cooled, the mixture was poured into ice-water and the resulting precipitate was collected by filtration and dissolved in methylene chloride. The solution was treated successively with silica gel (1 g) and activated charcoal and evaporated in vacuo. The crystalline residue was recrystallized from a mixture of ethyl acetate and n-hexane to give 8-(2-methoxybenzyloxy)-2-methyl-3-(2-propynyloxymethyl)imidazo[1,2-a]pyridine (1.85 g).

mp: 107° to 108° C.

NMR (CDCl$_3$, δ): 2.40–2.60 (1H, m), 2.50 (3H, s), 3.85 (3H, s), 4.06 (2H, d, J=2 Hz), 4.86 (2H, s), 5.36 (2H, s), 6.40–6.73 (2H, m), 6.91 (2H, t, J=8 Hz), 7.27 (1H, m), 7.50 (1H, b.d, J=8 Hz), 7.72 (1H, dd, J=15 Hz, 6 Hz).

Example 7

The following compound was prepared according to a similar manner to that of Example 6.

2-Methyl-8-(2-nitrobenzyloxy)-3-(2-propynyloxymethyl)imidazo[1,2-a]pyridine mp: 145° to 146° C. (recrystallized from a mixture or ethyl acetate and n-hexane).

NMR (CDCl$_3$, δ): 2.53 (3H, s), 2.43–2.70 (1H, m), 4.10 (2H, d, J=2 Hz), 4.90 (2H, s), 5.73 (2H, s), 6.33–6.83 (2H, m), 7.23–8.06 (4H, m), 8.16 (1H, dd, J=2 Hz, 8 Hz).

Example 8

The following compounds were prepared according to a similar manner to that of Example 4.

(1) 8-(2,6-Dimethyl-3-nitrobenzyloxy)-2-methyl-3-(2-propynyl)imidazo[1,2-a]pyridine mp: 147° to 149° C. (recrystallized from a mixture of ethyl acetate and n-hexane).

IR (Nujol): 3290, 1540, 1505, 1410, 1345, 1275, 1080 cm$^{-1}$.

NMR (CDCl$_3$, δ): 2.30 (1H, t, J=3 Hz), 2.43 (3H, s), 2.50 (3H, s), 2.53 (3H, s), 3.78 (2H, d, J=3 Hz), 5.30 (2H, s), 6.68 (1H, dd, J=2 Hz, 7.5 Hz), 6.80 (1H, t, J=7.5 Hz), 7.20 (1H, d, J=8 Hz), 7.73 (1H, d, J=8 Hz), 7.83 (1H, dd, J=2 Hz, 7.5 Hz).

Analysis Calcd. for C$_{20}$H$_{19}$N$_3$O$_3$: C 68.75; H 5.48; N 12.03. Found: C 69.05; H 5.32; N 11.73.

(2) 2-Methyl-8-(2-methyl-6-nitrobenzyloxy)-3-(2-propynyl)imidazo[1,2-a]pyridine mp: 177° to 178° C. (recrystallized from ethyl acetate).

IR (Nujol): 1540, 1510, 1280 cm$^{-1}$.

NMR (CDCl$_3$, δ): 2.03 (1H, t, J=3 Hz), 2.40 (3H, s), 2.53 (3H, s), 3.72 (2H, d, J=3 Hz), 5.43 (2H, s), 6.45–6.77 (2H, m), 7.25–7.46 (2H, m), 7.53–7.77 (2H, m).

(3) 2-Methyl-8-(4-methyl-3-pyridylmethoxy)-3-(2-propynyl)imidazo[1,2-a]pyridine mp: 127° to 128° C. (recrystallized from ethyl acetate).

IR (Nujol): 3240, 1600, 1565, 1540, 1495, 1285 cm$^{-1}$.

NMR (CDCl$_3$, δ): 2.04 (1H, t, J=3 Hz), 2.43 (6H, s), 3.73 (2H, d, J=3 Hz), 5.26 (2H, s), 6.47 (1H, dd, J=2 Hz, 7.5 Hz), 6.50–6.74 (1H, m), 7.05 (1H, d, J=5 Hz), 7.65 (1H, dd, J=2 Hz, 6 Hz), 8.35 (1H, d, J=5 Hz), 8.50 (1H, s).

(4) 2-Methyl-8-(2-methyl-3-nitrobenzyloxy)-3-(2-propynyl)imidazo[1,2-a]pyridine mp: 191° to 192° C. (recrystallized from methanol).

IR (Nujol): 3170, 1540, 1505, 1345, 1280, 1095 cm$^{-1}$.

NMR (CDCl$_3$, δ): 2.04 (1H, t, J=3 Hz), 2.45 (3H, s), 2.50 (3H, s), 3.75 (2H, d, J=3 Hz), 5.33 (2H, s), 6.42 (1H, dd, J=2 Hz, 7.5 Hz), 6.65 (1H, t, J=7.5 Hz), 7.10–7.35 (1H, m), 7.53–7.77 (3H, m).

(5) 2-Methyl-8-(2-methyl-5-nitrobenzyloxy)-3-(2-propynyl)imidazo[1,2-a]pyridine mp: 203° to 205° C. (recrystallized from methanol).

IR (Nujol): 3270, 1540, 1345, 1285 cm$^{-1}$.

NMR (DMSO-d$_6$, δ): 2.33 (3H, s), 2.48 (3H, s), 2.93 (1H, t, J=3 Hz), 3.90 (2H, d, J=3 Hz), 5.38 (2H, s), 6.70–6.93 (2H, m), 7.48 (1H, d, J=8 Hz), 7.80–7.93 (1H, m), 8.07 (1H, dd, J=2 Hz, 8 Hz), 8.31 (1H, d, J=2 Hz).

What we claim is:

1. An imidazopyridine compound of the formula:

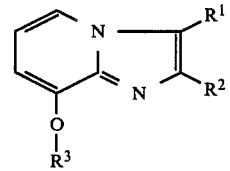

wherein
R$^1$ is lower alkynyl or lower alkynyloxy(lower)alkyl,
R$^2$ is lower alkyl, and
R$^3$ is mono(or di or tri)phenyl(lower)alkyl substituted by lower alkoxy, lower alkylthio, nitro or lower alkanesulfonyl, mono(or di or tri)phenyl(lower)alkyl substituted by nitro and one or two additional substituent(s) selected from nitro and lower alkyl, heterocyclic(lower)alkyl in which the heterocyclic moiety is selected from thienyl, furyl, pyrrolyl, pyrazolyl, thiazolyl, thiadiazolyl, triazolyl, pyridyl, pyridazinyl or triazinyl, or said heterocyclic(lower)alkyl substituted by at least one substituent selected from the group consisting of lower alkyl, lower alkoxy, and lower alkanamido, and a pharmaceutically acceptable salt thereof.

2. A compound of claim 1, wherein
$R^3$ is phenyl(lower)alkyl substituted by lower alkoxy, lower alkylthio, nitro or lower alkanesulfonyl.

3. A compound of claim 2, wherein
$R^3$ is benzyl substituted by methoxy, methylthio, nitro or mesyl.

4. A compound of claim 3, which is selected from a group consisting of:
8-(2-methoxybenzyloxy)-2-methyl-3-(2-propynyl)imidazo[1,2-a]pyridine,
2-methyl-8-(2-methylthiobenzyloxy)-3-(2-propynyl)imidazo[1,2-a]pyridine,
2-methyl-8-(2-nitrobenzyloxy)-3-(2-propynyl)imidazo[1,2-a]pyridine,
8-(2-mesylbenzyloxy)-2-methyl-3-(2-propynyl)imidazo[1,2-a]pyridine,
8-(2-methoxybenzyloxy)-2-methyl-3-(2-propynyloxymethyl)imidazo[1,2-a]pyridine, and
2-methyl-8-(2-nitrobenzyloxy)-3-(2-propynyloxymethyl)imidazo[1,2-a]pyridine.

5. A compound of claim 4, which is
8-(2-methoxybenzyloxy)-2-methyl-3-(2-propynyl)imidazo[1,2-a]pyridine.

6. A compound of claim 4, which is
8-(2-methoxybenzyloxy)-2-methyl-3-(2-propynyloxymethyl)imidazo[1,2-a]pyridine.

7. A compound of claim 1, wherein
$R^3$ is phenyl(lower)alkyl substituted by nitro and one or two additional substituent(s) selected from nitro and lower alkyl.

8. A compound of claim 7, wherein
$R^3$ is benzyl substituted by nitro and one or two additional substituent(s) selected from nitro and methyl.

9. A compound of claim 8, which is selected from a group consisting of:
8-(2,6-dimethyl-3-nitrobenzyloxy)-2-methyl-3-(2-propynyl)imidazo[1,2-a]pyridine,
2-methyl-8-(2-methyl-6-nitrobenzyloxy)-3-(2-propynyl)imidazo[1,2-a]pyridine,
2-methyl-8-(2-methyl-3-nitrobenzyloxy)-3-(2-propynyl)imidazo[1,2-a]pyridine, and
2-methyl-8-(2-methyl-5-nitrobenzyloxy)-3-(2-propynyl)imidazo[1,2-a]pyridine.

10. A compound of claim 1, wherein
$R^3$ is 3 to 7 membered heteromonocyclic(lower)alkyl in which the heterocyclic moiety is selected from thienyl, furyl, pyrrolyl, pyrazolyl, thiazolyl, thiadiazolyl, triazolyl, pyridyl, pyridazinyl or triazinyl, or is said heterocyclic(lower)alkyl substituted by at least one substituent selected from the group consisting of lower alkyl, lower alkoxy and lower alkanamido.

11. A compound of claim 10, wherein
$R^3$ is thienyl substituted by methyl, thiazolyl having acetamido or pyridyl which is unsubstituted or is substituted by methyl or methoxy.

12. A compound of claim 11, which is selected from a group consisting of:
2-methyl-8-(3-methyl-2-thienylmethoxy)-3-(2-propynyl)imidazo[1,2-a]pyridine,
2-methyl-3-(2-propynyl)-8-(3-pyridylmethoxy)imidazo[1,2-a]pyridine,
2-methyl-8-(3-methyl-4-pyridylmethoxy)-3-(2-propynyl)imidazo[1,2-a]pyridine,
2-methyl-8-(2-methyl-3-pyridylmethoxy)-3-(2-propynyl)imidazo[1,2-a]pyridine,
2-methyl-8-(3-methyl-2-pyridylmethoxy)-3-(2-propynyl)imidazo[1,2-a]pyridine,
8-(2-acetamidothiazol-4-ylmethoxy)-2-methyl-3-(2-propynyl)imidazo[1,2-a]pyridine,
8-(3,5-dimethyl-4-methoxy-2-pyridylmethoxy)-2-methyl-3-(2-propynyl)imidazo[1,2-a]pyridine, and
2-methyl-8-(4-methyl-3-pyridylmethoxy)-3-(2-propynyl)imidazo[1,2-a]pyridine.

13. A pharmaceutical composition which comprises, as an active ingredient, an antiulcerative effective amount of a compound of claim 1 or a pharmaceutically acceptable salt thereof in admixture with a pharmaceutically acceptable carrier.

14. A method for the treatment of a human or animal patient subject to ulcer which comprises administering an antiulcerative effective amount of a compound of claim 1 or a pharmaceutically acceptable salt thereof to said human or animal patient.

* * * * *